(12) United States Patent
Hansen

(10) Patent No.: US 11,045,430 B2
(45) Date of Patent: *Jun. 29, 2021

(54) METHOD FOR PREPARING ELECTROSPUN FIBERS WITH A HIGH CONTENT OF A BIOADHESIVE SUBSTANCE

(71) Applicant: Afyx Therapeutics A/S, Copenhagen (DK)

(72) Inventor: Jens Hansen, Copenhagen (DK)

(73) Assignee: AFYX Therapeutics A/S, København S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/395,956

(22) Filed: Apr. 26, 2019

(65) Prior Publication Data
US 2019/0254986 A1  Aug. 22, 2019

Related U.S. Application Data

(63) Continuation of application No. PCT/DK2018/050010, filed on Jan. 22, 2018.

(30) Foreign Application Priority Data

Jan. 23, 2017 (DK) ............................. PA 201770043

(51) Int. Cl.
| | |
|---|---|
| *A61K 9/70* | (2006.01) |
| *A61K 9/00* | (2006.01) |
| *A61K 31/575* | (2006.01) |
| *A61K 47/32* | (2006.01) |
| *A61K 47/34* | (2017.01) |
| *D01D 5/00* | (2006.01) |
| *D01F 6/16* | (2006.01) |
| *D01F 6/26* | (2006.01) |
| *D01F 6/62* | (2006.01) |
| *C08L 33/14* | (2006.01) |
| *C08L 39/06* | (2006.01) |
| *A61K 31/573* | (2006.01) |

(52) U.S. Cl.
CPC .............. *A61K 9/70* (2013.01); *A61K 9/006* (2013.01); *A61K 31/575* (2013.01); *A61K 47/32* (2013.01); *A61K 47/34* (2013.01); *D01D 5/003* (2013.01); *D01F 6/16* (2013.01); *D01F 6/26* (2013.01); *D01F 6/625* (2013.01); *A61K 31/573* (2013.01); *C08L 33/14* (2013.01); *C08L 39/06* (2013.01); *C08L 2203/02* (2013.01)

(58) Field of Classification Search
CPC ........ A61K 9/70; A61K 9/006; A61K 31/575; A61K 47/32; A61K 47/34; A61K 31/573; D01D 5/003; D01F 6/16; D01F 6/26; D01F 6/625; C08L 33/14; C08L 39/06; C08L 2203/02

See application file for complete search history.

(56) References Cited

U.S. PATENT DOCUMENTS

| | | |
|---|---|---|
| 7,390,760 B1 | 6/2008 | Chen et al. |
| 10,052,291 B2 | 8/2018 | Hansen et al. |
| 2003/0017208 A1 | 1/2003 | Ignatious et al. |
| 2003/0069369 A1 | 4/2003 | Belenkaya et al. |
| 2005/0215727 A1 | 9/2005 | Feldstein et al. |
| 2006/0013869 A1 | 1/2006 | Ignatious et al. |
| 2009/0269392 A1 | 10/2009 | Tauber et al. |
| 2010/0190254 A1 | 7/2010 | Chian et al. |
| 2010/0254961 A1 | 10/2010 | Nishio et al. |
| 2010/0323573 A1 | 12/2010 | Chu et al. |
| 2011/0045041 A1 | 2/2011 | Golubovic-Liakopolous et al. |
| 2011/0111012 A1 | 5/2011 | Pepper et al. |
| 2013/0295143 A1 | 11/2013 | Trout et al. |
| 2014/0128345 A1 | 5/2014 | Woodrow et al. |
| 2016/0166959 A1 | 6/2016 | Cui et al. |
| 2017/0119690 A1 | 5/2017 | Hansen et al. |
| 2018/0221295 A1 | 8/2018 | Hansen et al. |
| 2018/0325834 A1 | 11/2018 | Hansen et al. |

(Continued)

FOREIGN PATENT DOCUMENTS

| | | |
|---|---|---|
| CN | 2134635 A1 | 5/1995 |
| CN | 102251317 A | 11/2011 |
| EP | 2810645 A1 | 12/2014 |

(Continued)

OTHER PUBLICATIONS

International Search Report dated Jul. 23, 2015 in application No. PCT/EP2015/062842, 11 pages.
International Search Report issued by the International Searching Authority for Application No. PCT/EP2016/078151 dated Feb. 2, 2017, 6 pages.
International Preliminary Report on Patentability in PCT/EP2016/078151 dated Oct. 19, 2017, 6 pages.
International Search Report and Written Opinion issued by the International Searching Authority for Application No. PCT/DK2018/050010, dated Mar. 27, 2018, 12 pages.
Second Written Opinion issued by the International Searching Authority for Application No. PCT/DK2018/050010, dated Dec. 19, 2018, 7 pages.

(Continued)

*Primary Examiner* — Abigail Vanhorn
(74) *Attorney, Agent, or Firm* — Cooley LLP

(57) ABSTRACT

The present invention relates to a method for preparing electrospun fibers, the method comprising v) dissolving a fiber-forming hydrophilic polymer in an alcohol selected from C1-C3 alcohols, vi) dissolving a bioadhesive substance in water, wherein the bioadhesive substance has a solubility in water of 3 g/100 ml or more at 25° C. or g/100 ml or more at 25° C., and wherein the bioadhesive substance has a solubility in an alcohol selected from C1-C3 alcohols of 0.5 g/100 nil 10 or less at 25° C. or 0.1 g/100 ml or less at 25° C., vii) adding under stirring the resulting solution from ii) to the resulting solution from i), whereby the bioadhesive substance precipitates and a homogeneous suspension is formed, wherein the bioadhesive substance is suspended as particles, and viii) electrospinning the homogeneous suspension to obtain hydrophilic fibers.

19 Claims, 1 Drawing Sheet

(56) References Cited

U.S. PATENT DOCUMENTS

2019/0254985 A1* 8/2019 Hansen .................. A61K 47/32

FOREIGN PATENT DOCUMENTS

| | | |
|---|---|---|
| EP | 2813212 A1 | 12/2014 |
| JP | 2003-521493 A | 7/2003 |
| JP | 2005-290610 A | 10/2005 |
| JP | 2005-534716 A | 1/2006 |
| JP | 2006-502136 A | 1/2006 |
| JP | 2010-159268 A | 7/2010 |
| KR | 2005-0055696 A | 6/2005 |
| KR | 10-0564366 B1 | 4/2006 |
| RU | 94039534 A | 8/1996 |
| WO | WO 2001/27365 A1 | 4/2001 |
| WO | WO 2001/54667 A1 | 8/2001 |
| WO | WO 2004/014304 A2 | 2/2004 |
| WO | WO 2004/014448 A1 | 2/2004 |
| WO | WO 2002/076425 A2 | 10/2004 |
| WO | WO 2006/106514 A2 | 10/2006 |
| WO | WO 2010/099292 A2 | 9/2010 |
| WO | WO 2014/066297 A1 | 5/2014 |
| WO | WO 2015/189212 A1 | 12/2014 |
| WO | WO 2015/106342 A1 | 7/2015 |
| WO | WO 2015/186101 A1 | 12/2015 |
| WO | WO-2015189212 A1 * 12/2015 ............. A61K 47/10 |  |

OTHER PUBLICATIONS

International Preliminary Report on Patentability issued by the International Searching Authority for Application No. PCT/DK2018/050010, dated Apr. 9, 2019, 11 pages.

Ignatova et al.,Electrospinning of poly(vinyl pyrrolidone)-iodine complex and poly(ethylene oxide)/poly( vinyl pyrrolidone)-iodine complex—a prospective route to antimicrobial wound dressing materials European Polymer Journal, 43:1609-1623 (2007).

Son et. al., "The effects of solution properties and polyelectrolyte on electrospinning of ultrafine poly(ethylene oxide) fibers," Polymer, 45:2959-2966 (2004).

Dow Polyox product page https://www.industrialcellulosics. com/polyox 2018, retrieved Apr. 25, 2019, from https/www.industrialcellulosics.com/polyox.

Saraswathi et al., "Polymers in Mucoadhesive Drug Delivery System—Latest Updates," International Journal of Pharmacy and Pharmaceutical Sciences 5(3):423-430 (2013).

Alborzi et al., "Release of folic acid from sodium alginate-pectin-poly ethylene oxide electrospun fibers under in vitro conditions," LWT—Food Science and Technology, vol. 59, pp. 383-388 (2014) (avail. online Jun. 2014).

Chou et al., "Current strategies for sustaining drug release from electrospun nanofibers," Journal of Controlled Release, vol. 220, pp. 584-591 (2015) (avail. online Sep. 2015).

Illangakoon et al., "5-Fluorouracil loaded Eudragit fibers prepared by electrospinning" International Journal of Pharmaceutics (2015) vol. 495:895-902 (2015).

Unnithan et al., "Wound-dressing materials with antibacterial activity from electrospun polyurethane-dextran nanofiber mats containing ciprofloxacin HC1." Carbohydrate Polymers, 90(4):1786-1793 (2012).

Tonglairoum et al., "Fast-Acting Clotrimazole Composited PVP/HP[beta] CD Nanofibers for Oral Candidiasis Application," Pharmaceutical Research, 31(8):1893-1906 (2014).

Wongsasulak et al., "Effect of entrapped [alpha]-tocopherol on mucoadhesivity and evaluation of the release, degradation, and swelling characteristics of zein-chitosan composite electrospun fibers," Journal of Food Engineering, 120:110-117 (2014).

Li et al., "Electrospun polyvinyl-alcohol nanfibers as oral fast-dissolving delivery system of caffeine and riboflavin," Colloids and Surfaces, 103:182-188 (2012).

Tyagi et al., "ElectrospunNanofiber Matrix with a Mucoadhesive Backing Film for Orarnucosal Drug Delivery," International Journal of Materials, Mechanics and Manufacturing, 2(1):81-85 (2014).

Xin et al., "Fluorescent poly(p-phenylene vinylene)/poly(ethylene oxide) nanofibers obtained by electrospinning," Journal of Polymer Research, Kluwer Academic Publishers-Consultants Bureau, NL 18(4):477-482 (2010).

Database WPI Section Ch, Week 201227 Thomson Scientific, London, GB; Class A96, AN 2011-Q34326 XP002773634, Nie W; Shen X; Yu D; Zhul: "Preparation of electrospinning fiber for controlling release of alcohol-soluble medicine by dissolving zein and polyvinylpyrrolidone into ethanol aqueous solution, adding medicine, mixing, and conducting electrostatic spinning", & CN 102 251 317 A ((UYDG) Univ Donghua) Nov. 23, 2011 (Nov. 23, 2011), 2 pages.

Written Opinion issued by Singapore Patent Office for Application No. 11201800360Q, dated Apr. 4, 2019, 8 pages.

Extended European Search Report issued by the European Patent Office for Application No. 19205743.8, dated Jan. 31, 2020, 10 pages.

Santocildes-Romero et al., "Development of bioadhesive electrospun membranes for oral mucosal drug delivery," Biobarriers 2016 poster—Final, dated Mar. 7, 2016, 1 page.

Santocildes-Romero et al., "Novel Electrospun Bioadhesive Oral Patches for Mucosal Drug Delivery," EAOM 2016 Poster—Final, dated Sep. 15, 2016, 1 page.

Santocildes-Romero, et al., "Development of Electrospun Mucoadhesive Patches for Therapeutical Applications in Oral Medicine," UKSB 2017 Poster—Final , dated Jun. 20, 2017, 1 page.

Hadley et al., "Pre-clinical Evaluation of Novel Electrospun Patches for Intra-Oral Drug Delivery," A02_Murdoc Poster, dated Sep. 16, 2016, 1 page.

Colley et al., "Adhesion and Acceptability of Novel Oral Patches in Human Volunteers," EAOM Poster—Final dated Sep. 15, 2016, 1 page.

Clitherow et al.,"Development of Electrospun Polymer Devices for Drug Delivery to the Oral Mucosa," 2Warwickpolymerconference_KClitherow, dated Jul. 11, 2016, 1 page.

Clitherow et al., "Incorporating Antifungal Agents in Electrospun Patches to Inhibit Candida Albicans," KClitherow_PPE_China-17, dated Jul. 25, 2017, 1 page.

Masek et al.,"Multi-layered nanofibrous mucoadhesive films for buccal and sublingual administration of drug-delivery and vaccination nanoparticles—important step towards effective mucosal vaccines", Journal of Controlled Release, Elsevier, Amsterdam, NL 249:183-195 (2017).

* cited by examiner

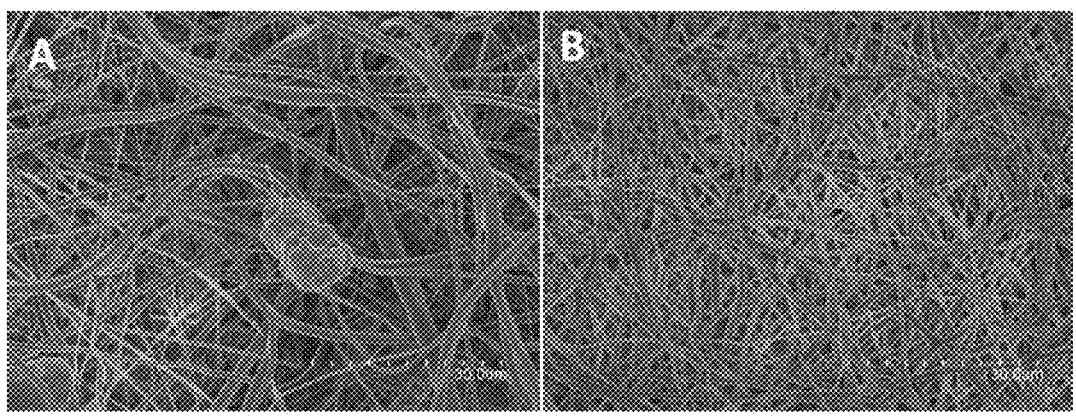

METHOD FOR PREPARING ELECTROSPUN FIBERS WITH A HIGH CONTENT OF A BIOADHESIVE SUBSTANCE

CROSS-REFERENCE TO RELATED APPLICATIONS

This application is a continuation of International Application No. PCT/DK2018/050010, filed Jan. 22, 2018, and claims the benefit of priority to Denmark Patent Application PA 2017 70043, filed Jan. 23, 2017, the contents of each of which are herein incorporated by reference in their entirety.

FIELD OF THE INVENTION

The present invention relates to bioadhesive electrospun fibers having a high content of a bioadhesive substance, ie the concentration of the bioadhesive substance in the fibers is 30% w/w or more—on a dry basis. The fibers are used in pharmaceutical or cosmetic compositions for application to a mucosa or skin, notable the oral mucosa, to deliver a drug substance to the systemic circulation via the oral mucosa or skin.

BACKGROUND OF THE INVENTION

Many substances have bioadhesive properties. In the preparation of electrospun fibers having a content of a bioadhesive substance a challenge is to balance the individual components in order to enable incorporation of a bioadhesive substance in an amount that is sufficient to obtain adhesion to mucosa or skin for a desired period of time and also to ensure that the fibers (eg in the form of a pharmaceutical or cosmetic composition) do not release or disconnect from the application site.

The present invention is a further development of the applicant's previous patent application published as WO 2015189212 relating to bioadhesive electrospun fibers. From this publication, it is clear that eg polyethylene oxide (PEO) may be used as a bioadhesive substance and due to its adhesive properties as well as solubility properties, high molecular weight polyethylene oxides are preferred such as polyethylene oxides having a molecular weight of 2,000,000 Daltons. The electrospinning process described in WO 2015189212 involves the use of one solvent in which the hydrophilic fiber-forming polymer is soluble whereas the bioadhesive substance is not soluble and is added to the solvent in solid form.

Xin et al: Flurorescent poly(p-phenylene vinylen)/poly (ethylene oxide) nanofibers obtained by electrospinning, Journal or Polymer Research vol. 18, No.4, 27 Apr. 2010 relates to fluorescent PPV/PEO nanofibers obtained by electrospinning. PPV is a hydrophobic polymer. The present invention relates to hydrophilic fiber-forming polymers.

DESCRIPTION OF THE INVENTION

The present invention addresses these problems by providing a method for preparing electrospun fibers comprising adding a solution of the bioadhesive substance(s) to a solution of the hydrophilic fiber-forming polymer(s), which addition result in precipitation of the bioadhesive substance.

Thus, the present invention provides a method for preparing electrospun fibers, the method comprising i) dissolving a fiber-forming hydrophilic polymer in an alcohol selected from C1-C3 alcohols,
ii) dissolving a bioadhesive substance in water, wherein the bioadhesive substance has a solubility in water of 3 g/100 ml or more at 25° C. or 10 g/100 ml or more at 25° C., and wherein the bioadhesive substance has a solubility in an alcohol selected from C1-C3 alcohols of 0.5 g/100 ml or less at 25° C. or 0.1 g/100 ml or less at 2.5° C.
iii) adding under stirring the resulting solution from ii) to the resulting solution from i), whereby the bioadhesive substance precipitates and a homogeneous suspension is formed, wherein the bioadhesive substance is suspended as particles, and
iv) electrospinning the homogeneous suspension to obtain hydrophilic fibers.

Thus, the present invention is based on the solubility differences of the bioadhesive substance(s) in water—where it is soluble—and in alcohol—where it precipitates. As seen from above, the water content in the alcohol in step i) must be relatively low; this is due to the fact that the hydrophilic polymer(s) is(are) soluble in alcohol, and care should be taken that the final content of water in the suspension that is ready for electrospinning must not exceed 20-50% w/w as the hydrophilic fiber-forming polymer normally swells in water or aqueous medium and it is important to control the swelling to avoid a suspension that has a viscosity that is too thick so that the suspension cannot be delivered through a needle without clotting it resulting in no fibers formed. If the amount of water corresponds eg to 50% w/w then it is contemplated that the spinning process is initiated shortly (within 30 min to 1 hour) after mixing of the ethanol and aqueous solution to avoid swelling.

Thus, the solubility of the hydrophilic fiber-forming polymer(s) in an alcohol as well as in the resulting alcoholic-water mixture is important. The solubility of the hydrophilic polymer in an alcohol and in the resulting alcoholic-water mixture is 3 g/100 ml or more at 25° C. or 10 g/100 ml or more at 25° C.

Moreover, the solubility of the bioadhesive substance in the resulting alcoholic-water mixture is 0.5 g/100 ml or less at 25° C. or 0.1 g/100 ml or less at 25° C.

A drug substance may be included in step i) or ii) of the method dependent on its solubility.

Although eg polyethylene oxide with a molecular weight of 2,000,000 daltons has excellent bioadhesive properties, the present inventors have found that the electrospinning process is not optimal, when PEO 2,000,000 is used. Due to the high molecular weight of PEO, which relates to relatively long chains of PEO, PEO 2,000,000 tends to mix with the fiber-forming hydrophilic polymer in the fibers, but due to the chain length the distribution of PEO 2,000,000 in the fibers may be too random eg due to a small surface area of PEO 2,000,000. To alleviate this and in order to obtain a more even distribution, experiments with micronized PEO 2,000,000 have been made. However, it has not been possible to obtain sufficiently small particle size of PEO 2,000,000. Thus, the needles used in the spinning process—when micronized PEO 2,000,000 is used—seems easily to be blocked and the resulting fibers seem to be less robust than desired.

Moreover, as seen from the example herein, even if the molecular weight of PEO is markedly reduced suspension of PEO in the alcoholic solvent together with the hydrophilic polymer(s) lead to an uneven distribution of PEO in the electrospun material. However, applying the method according to the invention, where PEO firstly is dissolved in water and then secondly, this aqueous solution is admixed with an alcoholic solution containing the hydrophilic polymer(s) to precipitate PEO, gives the desired results where PEO is evenly distributed on the fiber-material obtained by electrospinning. It is contemplated that PEO is not an intergral part of the fiber material, but is located as very fine particles on the fibers.

When the molecular weight of the bioadhesive substance is decreased compared with the disclosure in WO 2015/189212 it is contemplated that an increase in concentration of bioadhesive substance in the fibers is necessary in order to obtain a desired bioadhesion.

In order to achieve a strong bioadhesion, a bioadhesive substance must be used in the electrospun fibers in a relatively high concentration such as a concentration of 30% w/w. This further complicates the process of manufacturing the fibers.

Of specific interest is a composition made according to the invention and comprising an anti-inflammatory drug substance such as a corticosteroid. The corticosteroid may be selected from the group consisting of amcinonide, betamethasone, budenoside, clobetasol, clobetasone, cortisone, desonide, desoxycortisone, desoximethasone, dexamethasone, diflucortolon, diflorasone, flucortisone, flumethasone, flunisolide, fluocinonide, fluocinolon, fluorometholone, fluprednisolone, flurandrenolide, fluticasone, halcinonide, halobetasol, hydrocortisone, mepredni-sone, methylprednisone, mometasone, paramethasone, prednicarbate, prednisone, prednisolone and triamcinolone or a pharmaceutically acceptable ester or acetonide thereof. The corticosteroid may preferably be selected from betamethasone, budenoside, clobetasol, clobetasone, desoximethasone, diflucortolon, diflorasone, fluocinonide, fluocinolon, halcinonide, halobetasol, hydrocortisone, mometasone and triamcinolone or a pharmaceutically acceptable ester thereof. The corticosteroid ester may for instance be betamethasone acetate, betamethasone dipropionate, betamethasone valerate, clobetasol propionate, dexamethasone acetate, flumethasone pivalate, fluticasone propionate, hydrocortisone acetate, hydrocortisone butyrate or mometasone furoate. The acetonide may be selected from fluocinolone acetonide or triamcinolone acetonide. The corticosteroid is preferably betamethasone dipropionate, betamethasone valerate or clobetasol propionate. Preferred in the present context is clobetasol or a derivative thereof such as clobetasol propionate.

Corticosteroids are a class of steroid hormones that are produced in the adrenal cortex of vertebrates.

Corticosteroids may be used in the treatment of various conditions/diseases including i) allergy and respirology diseases such as asthma (severe exacerbations), chronic obstructive pulmonary disease (CPOD), allergic rhinitis, atopic dermatitis, hives, angioedema, anaphylaxis, food allergies, drug allergies, nasal polyps, hypersensitivity pneumonitis, sarcoidosis, eosinophilic pneumonia, and interstitial lung disease;

ii) Dermatology such as pemphigus vulgaris and contact dermatitis;

iii) Endocrinology including adrenal insufficiency and congenital adrenal hyperplasia;

iv) Gastroenterology including ulcerative colitis, Crohn's disease and autoimmune hepatitis;

v) Hematology such as lymphoma, leukemia, hemolytic anemia and idiopathic thrombocytopenic purpura;

vi) Rheumatology/Immunology including rheumatoid arthritis, systemic lupus erythematosus, Polymyalgia rheumatica, Polymyositis, Dermatomyositis, Polyarteritis and Vasculitis;

vii) Ophthalmology including uveitis and keratoconjunctivitis;

viii) Other conditions including multiple sclerosis, organ transplantation, nephrotic syndrome, chronic hepatitis (flare ups) and Cerebral edema.

Corticosteroids are normally divided into glucocorticoids and mineralocorticoids. In the present context, especially glucocorticoids are of interest. In the present context, the glucocorticoids of interest are those normally used in the treatment of diseases where it is possible in a relatively easy manner to apply a composition comprising the electrospun fiber. Regarding corticosteroids, many compositions are intended for application to the skin or a mucosa and such a composition may be applied i) directly to a mucosa such as the oral, nasal, rectal or vaginal mucosa, ii) directly to the skin iii) during transplantation to the transplanted tissue—provided the composition is provided in sterile form iv) during surgery to an infected or otherwise diseased area of the body v) directly on a wound—either an external or internal wound.

Other drug substances of interest in the present context are: pain-killers or antiesthetics (eg lidocaine, capsaicins), immune response modifiers (eg imiquimod), inflammatory diseases such as Lichen planus eg genital lichen planus including vulvovaginalginival syndrome.

However, it is contemplated that any drug substance may be included.

Hydrophilic Electrospun Layer

The hydrophilic polymer, which is the basic ingredient in the hydrophilic material, is the ingredient that has the ability to form a fiber material. In order to avoid any confusion with other ingredients present either in the electrospun fibers or in a composition thereof the term "fiber-forming hydrophilic polymer" is used. The fiber-forming hydrophilic polymer is suitably a polymer that is soluble in or forms a gel in a $C_1$-$C_3$ alkanol such as methanol, ethanol, propanol or isopropanol, notably ethanol, propanol or isopropanol, or in water mixtures thereof, where the water content is at the most 20% w/w, preferably much less such as at the most 5-10% w/w or 3-5% w/w. The spinning process requires that the polymer, which is the main component of the fibers, is in dissolved form to allow a steady stream of the dissolved polymer to flow from a needle to a grounded collecting plate in a jet-like fashion during the spinning process.

Suitable fiber-forming hydrophilic polymers are polyvinylpyrrolidone (PVP), acrylates and acrylic copolymers (eg Eudragit®), and mixtures thereof. Other polymers like eg ethylcellulose (EC), hydroxypropylcellulose (HPC), or mixtures thereof may also be used. Ethylcellulose (EC), hydroxypropylcellulose (HPC), or mixtures thereof may especially be used in combination with polyvinylpyrrolidone (PVP) and/or acrylates including acrylic copolymers (eg Eudragit®) In the examples especially PVP and acrylic copolymers have been used. Other hydrophilic polymers may be polyvinylalcohol and carboxymethylcellulose (including alkali salts thereof), and mixtures thereof.

Polyvinylpyrrolidone can be used in a grade having an approximate molecular weight of from 2,500 Da to 3,000,000 Da (eg Povidone with K-values of from 12 to 120). PVP can be purchased as Kollidon®:

| Kollidon ® | Weight average molecular weight $M_w$ |
|---|---|
| 12PF | 2,000-3,000 |
| 17PF | 7,000-11,000 |
| 25 | 28,000-34,000 |
| 30 | 44,000-54,000 |
| 90F | 1,000,000-1,500,000 |

In the low MW-range suitable grades are contemplated to have a MW of from about 25,000 to about 120,000 Da, notably from about 70,000 to about 100,000 Da. In the examples herein Kollidon® 90F has mainly be used and accordingly, a preferred PVP has a $M_w$ of from about 900,000-about 3,000,000, notably from about 1,000 to about 1,500,000.

Ethylcellulose is sold under the trademark ETHOCEL™ (Dow Chemical Company) and is available in many different grades. Dow Chemical Company produces ethylcellulose in two ethoxyl types (denoted Standard and Medium). Dependent on its ethoxyl content ethylcellulose may have different softening point and melting point temperatures. Ethylcellulose is also produced in a number of different viscosities. In the table below is given a listing of available ethylcelluloses.

| ETHOCEL polymers | | | |
|---|---|---|---|
| Product viscosity designation | Viscosity range mPa * s | Ethoxyl content % Standard 48.0-49.5 | Ethoxyl content % Medium 45.0-46.5 |
| 4 | 3-5.5 | ETHOCEL Std. 4 | |
| 7 | 6-8 | ETHOCEL Std. 7 | |
| 10 | 9-11 | ETHOCEL Std. 10 | |
| 14 | 12.6-15.4 | ETHOCEL Std. 14 | |
| 20 | 18.22 | ETHOCEL Std. 20 | |
| 45 | 41.49 | ETHOCEL Std. 45 | |
| 50 | 45-55 | | ETHOCEL Med. 50 |
| 70 | 63-77 | | ETHOCEL Med. 70 |
| 100 | 90-110 | ETHOCEL Std. 100 | ETHOCEL Med. 100 |
| 200 | 180-220 | ETHOCEL Std. 200 | |
| 300 | 270-330 | ETHOCEL Std. 300 | |
| 350 | 250-385 | ETHOCEL Std. 4 | |

In plasticized form it has excellent thermoplasticity and is useful for compositions made by molding, extrusion or lamination. Ethylcellulose is also an excellent film-former and is used in coating of eg tablets. The above-mentioned ethylcellulose qualities have an ethoxyl content of at least 45.0% and, accordingly they are soluble in ethanol and practically insoluble in water.

Acrylates and acrylic acid derivative include polymethacrylates, methacrylate copolymers, acrylic copolymers and methacrylate polymers. Preferred acrylates are those sold under the trademark EUDRAGIT®, which are soluble in ethanol, or acrylates/octaacrylamide copolymer (sold under the name DERMACRYL 79). These include EUDRAGIT®E 12,5 (amino methacrylate copolymer), EUDRAGIT® E100 (amino methacrylate copolymer; basic butylated methacrylate copolymer), EUDRAGIT®E PO ((amino methacrylate copolymer), EUDRAGIT®L 100-55, EUDRAGIT®L 100 (methacrylic acid-methyl methacrylate copolymer 1:1), EUDRAGIT®S 100 (methacrylic acid-methyl methacrylate copolymer 1:2), EUDRAGIT®RL 100, EUDRAGIT®RL 100 (ammonio methacrylate copolymer type A), EUDRAGIT®RL PO, EUDRAGIT®RS 100 (ammonio methacrylate copolymer type B), EUDRAGIT®RS PO, EUDRAGIT®E is a cationic polymer based on dim-ethylaminoethyl methacrylate and other neutral methacrylic acid esters: EUDRAGIT®L and S are methacrylic acid copolymers and are cationic copolymerization products of methacrylic acid and methyl methacrylate. EUDRAGIT®RL or RS is ammonio methacrylate copolymers synthesized from acrylic acid and methacrylic acid.

EUDRAGIT® E 100 is soluble up to pH 5.5 and E 12.5 is soluble above pH 5.

EUDRAGIT® L30 D-55, L-100-55 (methacrylic acid-ethyl acrylate copolymer 1:1), L 100, L 12,5, are normally used in enteric formulations, but may be used in order to delay release of the drug substance from fibers of the invention. EUDRAGIT® L30 D-55, and L-100-55 dissolve at a pH about 5.5 and the grades L 100 and L 12,5 dissolve at pH 6 or above.

As the pH in saliva normally is about 5-6 these polymers are of interest for fibers for oral use. If sustained or prolonged release is desired polymers being soluble at lower of higher pH may be more suitable for use.

EUDRAGIT® products are also available for sustained-release formulations and such grades may be of interest to incorporate in fibers of the invention either alone or together with another hydrophilic polymer. Relevant grades belong to the RL, RS, NE and NM series such as RL 100, RL PO, RL 30D, and RL 12,5, RS 100, RS PO, RS 30D, and RS 12,5, NE 30D and NE 40D, and NM 30D.

Hydroxypropylcellulose is a non-ionic water-soluble cellulose ether. It combines organic solvent solubility, thermoplasticity and surface activity and that thickening and stabilizing properties. The fibers are flexible and non-tacky at high humidity. Hydroxypropylcellulose is sold under the name KLUCEL™.

Carboxymethylcellulose is available in a broad selection of grades. The viscosity ranges from 10 to 100,000 mPa*s. It is also available as it's sodium salt with a broad range of substitution levels. Dow Chemical Company sells sodium carboxymethylcellulose under the name WALOCEL™.

Polyvinylalcohol can be used in grade having an approximately molecular weight of from 20,000 Da to 200,000 Da.

The preferred fiber-forming hydrophilic polymers are selected from PVP, hydroxypropylcellulose (HPC), acrylates and acrylic acid derivatives, and mixtures thereof.

The hydrophilic material, which is in the form of an electrospun fibrous layer, may also contain one or more drug substance, one or more bioadhesive substances, one or more pharmaceutically or cosmetically acceptable excipients. Such excipients include pH-adjusting agents, preservative, taste-masking agents, anti-oxidants, stabilisers, permeation enhancers etc. Moreover, dependent of the intended use other excipients may be present such as plasticizers, surfactants etc.

The concentration of the fiber-forming hydrophilic polymer(s) in the hydrophilic material according to the invention is normally up to 100% w/w. When other ingredients are included, the minimal concentration of the fiber-forming hydrophilic polymer(s) is generally about 25% w/w to ensure that fibers are formed containing all the ingredients. Notably, the concentration is from about 40% to about 92% w/w notably from about 50 to about 85% w/w or from about 60% to 75% w/w.

In those cases, where the composition is designed for use on a mucosal surface, it may be of interest to include a bioadhesive substance to promote adhesion to the mucosa.

If strong bioadhesion is desired, the concentration of bioadhesive substance in the electrospun fibers must be of a relatively high concentration such as 20% w/w or more, notably 40% w/w or more. To obtain fibers with such a high content of bioadhesive substance it is necessary to select bioadhesive substances that have a low solubility in the solvent used in the electrospinning process—if they are soluble, they will swell and make the electrospinning impossible or at least very difficult.

If mild bioadhesion is desired, the concentration of the bioadhesive substance in the electrospun fibers must be of a concentration of at the most 20% w/w or less, notably 10% w/w or less.

Fibers of the invention also contain a bioadhesive substance. In order to ensure an easy manufacture of the fibers and to obtain the desired bioadhesive properties in situ after application to the mucosa, it is important that the bioadhesive in itself does not contribute significantly to the viscosity of a solution containing the fiber-forming hydrophilic polymer.

In the present context, the term "bioadhesive" or "bioadhesion" indicates attachment to a specified biological location such as to the surface of the skin, a lip or a mucosal surface. A bioadhesive substance imparts broadhesiveness to the drug-containing fibers of the invention or, in certain cases it may be included in a composition of the invention eg as a separate layer, which—after application—is the inner layer facing the skin or mucosa, i.e. the layer that is in contact with the skin or mucosa.

The bioadhesive substance for use in the present context can be selected from dextran, polyethylene oxides, alginate, tragacanth, carrageenan, pectin, gelatin, guar, xanthan, gellan, methylcellulose, hydroxypropylmethylcellulose (HPMC), carboxymethylcellulose and alkali salts thereof, polymers of acrylic acids (PAA derivatives), chitosan, lectins, thiolated polymers, polyox WSRA, PAA-co-PEG (PEG is polyethylene glycol), and mixtures thereof.

In general, it is expected that the adhesive effect of polymers increases with increasing molecular weight. Thus, in general adhesive polymers having relatively high molecular weight are preferred.

Polyethylene oxide can be used in grade having an approximate molecular weight of from 100,000 to 4,000,000. Polyethylene oxide is sold under the name POLYOX™ (Dow Chemical Company) with molecular weights ranging from 100,000 to 700,000 Da. As mentioned herein before. PEO with molecular weights below 500,000 daltons are preferred, notably PEO having a molecular weight from about 100,000 to about 400,000 daltons such as polyethylene oxide having a molecular weight of about 200,000 daltons. This is due to the solubility issues discussed herein.

Similar considerations apply to the other bioadhesive substances mentioned herein. Experiments with eg dextran having height molecular weight have shown that micronization of dextrans also is difficult, i.e. it is difficult to obtain dextran in micronized form when the molecular weight is more than 1,000,000 daltons.

Dextran can be used in grade having an approximate molecular weight of from 400,000 Da to about 1,000,000 Da. Dextrans have a molecular weight of from about 400,000 to about 700,000 daltons.

Cellulose derivatives include hydroxypropylmethylcellulose, methylcellulose and carboxymethylcellulose.

Methylcellulose is sold under the name METHOCEL™ (Dow Chemical Company) and is available in a wide range of viscosity grades (from less than 3 to over 100,000 mPA*s).

HPMC is sold in various qualities depending on the viscosity. HPMC is sold under the names Metocel® and Klucel®. A suitable HPMC has an average molecular weight from about 80,000 to about 140,000.

Preferred bioadhesive substances are polyethylene oxides, dextrans or combinations thereof.

The hydrophilic material used in the fabrication of the two-layered product according to the invention may contain a drug substance. In principle, the drug substance may be any drug substance suitable for application to a mucosa or skin for the treatment of a disease or condition. Of particular interest are drug substances selected from drug substances, which are indicated for treatment of a disease of the skin, lip, or mucosa, or in the case, where the fibers are included in compositions for application on an internal surface as described here, the drug substance may be any drug substance that is indicated for the specific treatment. In the present context, the drug substance may be selected from drug substances, which are indicated for treatment of a disease in the oral cavity such as a drug substance that is indicated for local treatment of a disease in the oral cavity. The drug substance may be present in dissolved, undissolved or partly dissolved form dependent on the drug solubility in the hydrophilic polymer and bioadhesive substance used.

Hydrophobic Electrospun Layer and Method for Application to the Hydrophilic Electrospun Layer The hydrophobic material is a hydrophobic electrospun layer. Notably, it is water-impermeable eg to enable an occlusive effect and/or a protective effect against fluids such as body fluids. The latter is relevant in the case where the two-layered product is for use in particularly wet environments, where it is desirable to protect the drug substance(s) within the hydrophilic material from being dissolved into the fluids. Suitable materials for providing a water-impermeable coating include polyethylene-co-vinyl acetate, ethyl-cellulose, poly(caprolactone), carbothane or polysoftane.

As mentioned in connection with the hydrophilic material, the material may contain one or more acceptable excipients. The excipients mentioned under the hydrophilic material may also be used in the hydrophobic material and vice versa.

The hydrophilic fibers are prepared as a thin layer. A further electrospun layer of eg hydrophobic fiber-forming polymer(s) may be attached to the hydrophilic layer. This may be done by a method involving comprising pressure and heat is suitable for fabricating a two-layered product comprising a hydrophilic first material made from electrospun fibers connected to a hydrophobic second material made from electrospun fibers, and wherein said first material may contain a drug, and said method being characterized in that said method comprises using a press comprising a first surface and a second surface, and wherein said second surface has a temperature being higher than the temperature of said first surface, said first and second material being arranged in a layered combination between the first and second surface of the press, wherein a pressure is provided towards said layered combination from said first and second surface of said press, and whereby said first material comes into contact with said first surface of said press, wherein the combination of pressure between the first and second surface and the temperature of said second material connects said first and second material into said two-layered product.

By a layered combination is meant that the first material and the second material are arranged such that their primary planes are parallel, i.e. said materials are arranged on top of each other resembling a stack or a sandwich.

By a connection between the first material and the second material is meant any kind of connection, physical and/or chemical, ensuring said materials are not separated by accident. A physical connection may be entanglement among the electrospun fibers, whereas a chemical connection may be manifested as chemical bonds. It is contemplated that the connection is established by physical connection or weak interaction at the molecular level (ion-ion interaction, van der Waal's forces).

The heating of the hydrophobic second material by the second surface increases the strength of the bonding between the hydrophilic first and hydrophobic second material. More particular, by heating the polymer of the hydrophobic second material to a temperature of below the melting point of the polymer or, alternatively, to the melting point or above, but for a relatively short time to avoid totally melting of the polymer and adherence of the polymer to the second surface. By the subsequent cooling of the two-layered product through the termination of the heating, the hydrophilic and hydrophobic electrospun layers are locked in their new position.

The hydrophilic first material may contain a drug substance according to the invention, and an increased temperature of said hydrophilic first material may alter the properties of said drug. It is therefore desirable to avoid heating of said first hydrophilic material. However, this may depend upon the drug used.

The heating means may be any means capable of heating the surfaces of the press to a predefined temperature. The heating may originate from electrical resistance, hot fluids transferring heat to the surface, or any other heating means capable of being incorporated into a press as disclosed.

The material of the surface of the press in contact with the materials to be bonded may be any material not damaging the chemical composition of the electrospun fibers. Further, a material with excellent heat capacity for transferring heat and a material capable of withstanding high pressures is desired. Therefore, metal is the preferred material, but ceramics is foreseen within the scope of the invention as well.

In an embodiment, the press is a roller press with two counter-rotating rollers, also denote calender. The rollers may be driven by any machinery commonly used in the field of such presses. The two rollers are mutual parallel and aligned to have a gap of a size facilitating the pressure needed for bonding the first and second material into the two-layered product. The surface of one of the rollers is heated to a temperature being higher than the temperature of the surface of the other roller. Due to the rollers rotating in opposite directions of each other, an input is created where the surfaces of the two rollers converge into the gap, whereas an output is created where the surfaces of the two rollers diverge out of the gap. In order to achieve the two-layered product, the hydrophobic material and the hydrophilic material are arranged in a layered combination and fed into the input, such that the hydrophobic material comes into contact with the roller having a heated surface. Due to the rotation of the rollers, the size of the gap ensuring a sufficient pressure, and the temperature of the surfaces of the rollers, the two materials are bonded into the two-layered product and led out through the output of the rollers.

In an embodiment, the press is a plate press comprising a first and a second surface being substantially flat and mutually parallel. Said two mutually parallel surfaces are capable of retracting and moving closer relative to each other. One of said surfaces are heated to a temperature being higher than the temperature of the other surface. Prior to bonding, the first hydrophilic material and the second hydrophobic material to be bonded are arranged in between the two surfaces in a layered combination with the hydrophobic material to be in contact with the heated surface. By moving the first and second surfaces mutually closer, a pressure is applied onto the layered combination, and in combination with the temperature of the surfaces, the bonding occurs. Subsequently, the parallel surfaces are retracted and the two-layered product formed from the bonding is removed from the press. The press may be driven by hydraulics, but other machine presses are foreseen within the scope of the invention.

The press may be a combination of a flat surface and a roller arranged to roll across said surface. Either the surface of the roller or the flat surface is heated to a temperature being higher than the temperature of the opposite surface. The hydrophilic first material and the hydrophobic second material is arranged in a layered combination upon the flat surface, with the second hydrophobic material in contact with the heated surface. The roller is set to roll across said layered combination, applying a pressure sufficient for bonding the first and second material into the two-layered product. Either the pressure may be applied through the roller being set to a predefined distance above the flat surface, or it may be further forced down onto the layered combination by use of external mechanics, such as hydraulics.

In an embodiment, the hydrophobic material and the hydrophilic material are shaped into sheets or layers prior to the bonding process, wherein the thickness of said sheets is significantly smaller than any other dimension of the sheets.

The thickness of the hydrophilic and hydrophobic material need not be the same. The thicker the hydrophobic layer is the less flexible it is. Thus, in order to achieve a flexible layer, the hydrophobic layer is applied with a thickness that is the same or smaller than the hydrophilic layer. In those cases, where the function of the hydrophobic layer is to keep water or body fluid to enter the hydrophilic layer from via the hydrophobic layer, the layer must be sufficiently thick and robust to withstand the impact of water or body fluid. Normally, the hydrophobic layer is present in an amount 10-50 g per $m^2$. Normally a thickness of less than 100 μm is obtained.

There may also be situations where the hydrophobic material has a larger extension than the hydrophilic material such that the hydrophobic material also covers the edges of the hydrophilic material.

In an embodiment, both the first and the second surface of the press are heated to a predefined temperature, or both surfaces may have the capability of being heated. The temperature of the surfaces possesses a temperature difference.

Besides the excipients mentioned herein before, the hydrophobic and/or hydrophilic fibers may contain a plasticizer. The plasticizer imparts a certain plasticity to the fibers, it may facilitate the manufacturing process and/or improve the flexibility and processability of the polymer(s). Examples of suitable plasticizers are citric acid esters like acetyl triethyl citrate, tributyl citrate or triethylcitrate, castor oil, diacetylated monoglycerides, dibutyl sebacate, diethyl phthalate, sorbitol, glycerol or glycerol derivatives like triacetin or tributyrin, a cellulose derivative like cellulose nitrate, glycols like polyethylene glycols notably polyethylene glycols with a molecular weight from about 100 to about 1500, polyethylene glycol monomethyl ether, propylene glycol, or mixtures thereof.

LEGENDS TO FIGURES

The FIGURE. Electrospun membranes from: A) Original recipe solution and, B) Recipe according to the invention involving precipitation of PEO.

EXAMPLES

Solution Preparation and Electrospinning Process
a) Comparative Method of Preparing the Fibers:
Weight absolute alcohol. Add slowly during stirring 6.52 wt. % Kollidon 90F and 8.15 wt. % of EudragitRS100 (of alcohol amount). Continue stirring during 24 h. Add slowly while stirring 13.05 wt. % of Polyox WSR N-80 (PEO 200,000 Mw). Keep stirring until a homogeneous suspension is created. Final mixture has 27.72% of total solids (66% of the original recipe).

Process with a single needle injector (15 G) at 2 mL/h, 10 cm of distance between the tip of the needle and the collector and 13 kV difference during 3 hours. The final membrane (fiber layer) was of 147.4 g per m$^2$.

b) Recipe According to the Present Invention:
Weight absolute alcohol. Add slowly during stirring 8 wt. % Kollidon 90F and 10 wt. % of EudragitRS100 (of alcohol amount). Continue stirring during 24 h.

Weight distilled water. Add slowly during stirring 16 wt. % of Polyox WSR N-80 (PEO 200,000 Mw). Keep stirring during 24 h.

Add slowly alcoholic solution to water solution while stirring. Keep stirring until a homogeneous mixture is formed. Final mixture has 17% or total solids Process with multineedle injector (56 needles 20 G) at 110 mL/h, 19 cm of distance between the tip of the needle and the collector and 60 kV difference during several hours. The final membrane (fiber layer) was of 160 per m$^2$. A small piece of 12×5 cm was cutted for further analyses.

Membrane Morphological Characterization

Both membranes (fiber layers) were inspected by scanning electron microscopy. Samples were sputtered with a mixture of gold-palladium during 180 second and were observed in a Hitachi S4800 at an accelerating voltage of 5 kV and 8 mm of working distance.

The FIGURE shows images of both membranes took at 1500 magnification. Samples made according to the present invention had a smaller fiber diameter mainly due to the lower total solid content and the higher difference of voltage applied. The comparative sample showed big particles of PEO between the fibers as was previously observed.

The invention claimed is:

1. A layered pharmaceutical composition comprising:
 a hydrophilic electrospun fiber layer, wherein the hydrophilic electrospun fibers comprise:
  clobetasol propionate;
  polyvinylpyrrolidone;
  an ammonio methacrylate copolymer type B; and
  about 35% to about 60% by weight polyethylene oxide (PEO) having a molecular weight of about 100,000 to about 400,000 daltons, and
 a hydrophobic layer comprising poly(caprolactone),
 wherein the hydrophilic electrospun fibers are formed by electrospinning a homogenous mixture of the clobetasol propionate, polyvinylpyrrolidone, ammonio methacrylate copolymer type B, and polyethylene oxide (PEO) in a $C_1$-$C_3$ alcohol containing 20-50% w/w water.

2. The layered pharmaceutical composition of claim 1, wherein the weight average molecular weight of the polyvinylpyrrolidone is about 900,000 Da to about 3,000,000 Da.

3. The layered pharmaceutical composition of claim 1, wherein the weight average molecular weight of the polyvinylpyrrolidone is about 1,500,000 Da.

4. The layered pharmaceutical composition of claim 1, wherein the amount of polyvinylpyrrolidone and ammonio methacrylate copolymer type B in the hydrophilic electrospun fiber layer is about 50% to about 65% by weight.

5. The layered pharmaceutical composition of claim 1, wherein the amount of polyvinylpyrrolidone and ammonio methacrylate copolymer type B in the hydrophilic electrospun fiber layer is about 45% to about 65% by weight.

6. The layered pharmaceutical composition of claim 1, wherein the amount of polyethylene oxide in the hydrophilic electrospun fiber layer is at least about 40% by weight.

7. The layered pharmaceutical composition of claim 1, wherein the amount of polyethylene oxide in the hydrophilic electrospun fiber layer is about 40% to about 55% by weight.

8. The layered pharmaceutical composition of claim 1, wherein the polyethylene oxide has a molecular weight of about 200,000 daltons.

9. The layered pharmaceutical composition of claim 1, wherein the hydrophilic electrospun fiber layer comprises:
 clobetasol propionate;
 about 40% to about 65% by weight polyvinylpyrrolidone (PVP) and an ammonio methacrylate copolymer type B; and
 about 35% to about 60% by weight polyethylene oxide having a molecular weight of about 100,000 to about 400,000 daltons.

10. The layered pharmaceutical composition of claim 1, wherein the hydrophilic electrospun fiber layer comprises:
 clobetasol propionate;
 about 45% to about 65% by weight polyvinylpyrrolidone (PVP) and an ammonio methacrylate copolymer type B; and
 about 35% to about 55% by weight polyethylene oxide having a molecular weight of about 100,000 to about 400,000 daltons.

11. The layered pharmaceutical composition of claim 1, wherein the hydrophilic electrospun fiber layer comprises:
 clobetasol propionate;
 about 45% to about 60% by weight polyvinylpyrrolidone and an ammonio methacrylate copolymer type B; and
 about 40% to about 55% by weight polyethylene oxide having a molecular weight of about 100,000 to about 400,000 daltons.

12. The layered pharmaceutical composition of claim 1, wherein the hydrophilic electrospun fiber layer comprises:
 clobetasol propionate;
 about 40% to about 60% by weight polyvinylpyrrolidone and an ammonio methacrylate copolymer type B; and
 about 40% to about 60% by weight polyethylene oxide having a molecular weight of about 100,000 to about 400,000 daltons.

13. The layered pharmaceutical composition of claim 1, wherein the hydrophilic electrospun fiber layer comprises:
 clobetasol propionate;
 about 40% to about 65% by weight polyvinylpyrrolidone and an ammonio methacrylate copolymer type B; and
 about 35% to about 60% by weight polyethylene oxide having a molecular weight of about 200,000 daltons.

14. The layered pharmaceutical composition of claim 1, wherein the hydrophilic electrospun fiber layer comprises:

clobetasol propionate;
about 45% to about 65% by weight polyvinylpyrrolidone and an ammonio methacrylate copolymer type B; and
about 35% to about 60% by weight polyethylene oxide having a molecular weight of about 200,000 daltons.

15. The layered pharmaceutical composition of claim 1, wherein the hydrophilic electrospun fiber layer comprises:
clobetasol propionate;
about 45% to about 60% by weight polyvinylpyrrolidone and an ammonio methacrylate copolymer type B; and
about 40% to about 55% by weight polyethylene oxide having a molecular weight of about 200,000 daltons.

16. The layered pharmaceutical composition of claim 1, wherein the hydrophilic electrospun fiber layer comprises:
clobetasol propionate;
about 40% to about 60% by weight polyvinylpyrrolidone and an ammonio methacrylate copolymer type B; and
about 40% to about 60% by weight polyethylene oxide having a molecular weight of about 200,000 daltons.

17. The layered pharmaceutical composition of claim 1, wherein the $C_1$-$C_3$ alcohol is ethanol.

18. The layered pharmaceutical composition of claim 1, wherein the $C_1$-$C_3$ alcohol contains about 50% w/w water.

19. The layered composition of claim 1, wherein the PEO is evenly distributed in the hydrophilic electrospun fibers.

\* \* \* \* \*